United States Patent [19]

Tokizawa et al.

[11] Patent Number: 4,925,953
[45] Date of Patent: May 15, 1990

[54] IMIDAZOLE DERIVATIVE

[75] Inventors: Minoru Tokizawa; Takemitsu Asaoka, both of Narita; Hideaki Matsuda, Abiko; Tatsuhiko Katori, Ibaraki, all of Japan

[73] Assignee: SS Pharmaceutical Co., Ltd., Tokyo, Japan

[21] Appl. No.: 277,308

[22] Filed: Nov. 29, 1988

[30] Foreign Application Priority Data

Dec. 9, 1987 [JP] Japan .................. 62-311576

[51] Int. Cl.$^5$ .................................. C07D 233/60
[52] U.S. Cl. .......................................... 548/341
[58] Field of Search .......................... 548/341

[56] References Cited

FOREIGN PATENT DOCUMENTS 2063260 6/1981 United Kingdom ............... 548/341

Primary Examiner—Richard A. Schwartz
Attorney, Agent, or Firm—Oblon, Spivak, McClelland, Maier & Neustadt

[57] ABSTRACT

Novel imidazole derivatives and their acid adducts are disclosed. The imidazole derivatives are represented by formula:

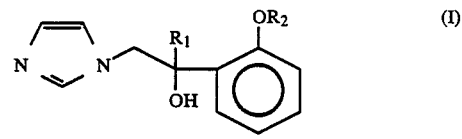

wherein $R_1$ represents an alkyl group, $R_2$ represents a hydrogen atom, an alkyl group which may have a substituent, or an aralkyl group which may have a substituent, provided that $R_1$ and $R_2$ are not both methyl groups at the same time. They have strong antimicrobial activity, especially against those fungi belonging to the genera Candida, Trichophyton, Microsporum, and Epidermorphyton, as well as against Gram-positive bacteria, and thus are useful as an antimicrobial agent.

4 Claims, No Drawings

IMIDAZOLE DERIVATIVE

BACKGROUND OF THE INVENTION

1. Field of the Invention

This invention relates to novel imidazole derivatives, and, more particularly, to novel imidazole derivatives having antimicrobial activities against Gram-positive bacteria, fungi, and the like.

2. Description of the Background

A number of imidazole derivatives having antimicrobial activities are conventionally known. Their antimicrobial activities, especially antifungal activities, are not necessarily satisfactory. Development of compounds having more effective activities are, therefore, required.

In view of this situation, the present inventors have undertaken extensive studies for the synthesis of various imidazole derivatives and for the detection of their pharmacological activities. As a result, the inventors have found that novel compounds represented by the following formula (I) exhibited strong antimicrobial activities, especially against Gram-positive bacteria, and fungi. This finding has led to the development and completion of this invention.

SUMMARY OF THE INVENTION

Accordingly, an object of this invention is to provide an imidazole derivative represented by formula (I):

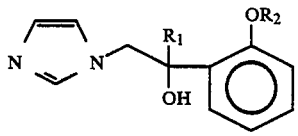

(I)

wherein $R_1$ represents an alkyl group, $R_2$ represents a hydrogen atom, an alkyl group which may have a substituent, or an aralkyl group which may have a substituent, provided that $R_1$ and $R_2$ are not both methyl groups at the same time; or an acid adduct thereof.

Other objects, features and advantages of the invention will hereinafter become more readily apparent from the following description.

DETAILED DESCRIPTION OF THE INVENTION AND PREFERRED EMBODIMENTS

Examples of alkyl groups represented by $R_1$ in formula (I) are linear, branched, or cyclic alkyl groups of a $C_{1-10}$ carbon atom content. Specific examples of especially preferable alkyl groups are methyl, ethyl, n-propyl, i-propyl, n-butyl, i-butyl, sec-butyl, t-butyl, pentyl, hexyl, octyl and cyclopropyl groups, and the like.

Alkyl groups for $R_2$ of formula (I) include, for example, linear, branched, or cyclic alkyl groups of a $C_{1-16}$ carbon atom content. Given as examples of aralkyl groups for $R_2$ of formula (I) are phenylalkyl groups and naphthylalkyl groups. The substituted groups for the alkyl group include, for example, a halogen atom, a lower alkoxy group, a lower alkanoyl group, a cyano group, and the like. When $R_2$ is an aralkyl group, the substituted groups for the aryl group of the aralkyl portion may be a halogen atom, a lower alkyl group, a lower alkoxy group, a lower alkanoyl group, a cyano group, and the like.

Among the compounds of formula (I) those having a hydrogen atom for $R_2$, i.e., Compound (Ia), can be prepared according to the following reaction formula, i.e., by reacting 1-(2-hydroxyphenacyl)imidazole (II) and a Grignard reagent (III). Compounds of formula (I) in which the $R_2$ is an alkyl or aralkyl group which may have a substituent, i.e., Compound (Ib), can be prepared by reacting Compound (Ia) with an alkylation or aralkylation reagent (IV) according to the following reaction formula:

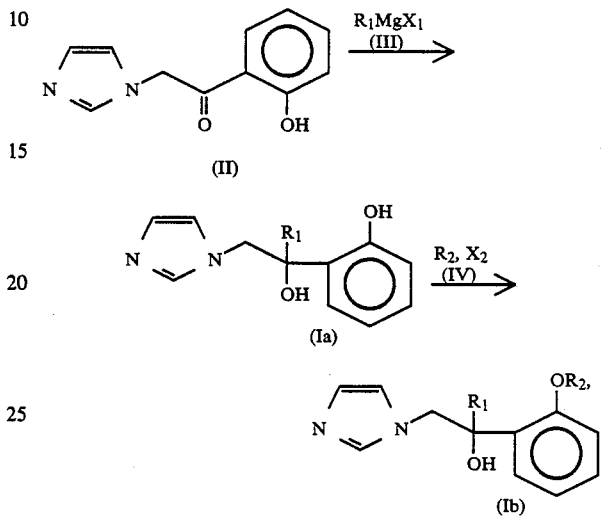

wherein $R_1$ has the meaning defined previously, $X_1$ and $X_2$ represent halogen atoms, and $R_2$, represents an alkyl or aralkyl group which may have a substituent.

The reaction for preparing Compound (Ia) is performed by using 1 to 5 moles of compound (III) for 1 mole of compound (II) in a solvent such as ether, tetrahydrofuran, or the like. The reaction is carried out at a temperature between 0° C. and the boiling point of the reaction mixture for 1 to several hours. After completion of the reaction, the surplus amount of compound (III) and addition salt produced in the reaction are decomposed using an aqueous solution of ammonium chloride, or the like. The mixture is extracted with a solvent such as chloroform or the like and, after evaporation of the solvent, pure Compound (Ia) can be obtained by silica gel chromatography or the like.

The reaction for the preparation of Compound (Ib) may be carried out using 1 to 2 moles of compound (IV) per one mole of Compound (Ia) in the presence of an alkali from room temperature to the boiling point of the solvent used, for 1 hour to 50 hours. Solvents which can be used include dimethylformamide, dimethylsulfoxide, acetone, ethanol, methanol, chloroform, methylene chloride, and the like. Given as examples of alkali which can be used in the reaction are sodium hydroxide, potassium hydroxide, sodium carbonate, potassium carbonate, and the like. After completion of the reaction, the reaction mixture is charged into water, and this mixture is extracted with a solvent such as ether or the like. After evaporation of the solvent, pure Compound (Ib) can be obtained by silica gel chromatography or the like.

The compound of formula (I) of this invention can be converted into an acid adduct through any conventional method. Given as examples of such acid adducts are those of pharmaceutically or medicinally permissible acids, including inorganic acids such as hydrochloric acid, sulfuric acid, nitric acid, hydrobromic acid and the like; and organic acids such as acetic acid, oxalic acid, fumaric acid, maleic acid, citric acid, malic acid, succinic acid, and the like.

Hereinafter are presented experimental examples to further illustrate the effectiveness of the invention. These examples are given for illustration of the invention and are not intended to be limiting thereof.

EXPERIMENTAL EXAMPLES

Antimicrobial activities of certain representative compounds of this invention, which had been obtained in the above-described manner, were investigated. Results are summarized in Table 1, in which the compound numbers correspond to those to be given in Examples which will be described herein.

TABLE 1

| Microorganism tested | Compound tested MIC ($\mu$g/ml) | |
| --- | --- | --- |
| | Compound 8 | Compound 59 |
| Bacillus subtilis ATCC 6633 | 3.12 | 6.25 |
| Staphylococcus aureus FDA 209P | 3.12 | 6.25 |
| Staphylococcus aureus Terajima | 3.12 | 6.25 |
| Staphylococcus aureus Smith | 3.12 | 6.25 |
| Staphylococcus epidermidis ATCC 12228 | 0.39 | 1.56 |
| Sarcina lutea ATCC 9341 | 0.20 | 0.05 |
| Streptococcus faecalis IFO 12964 | 6.25 | 6.25 |
| Micrococcus lysodeikticus IFO 3333 | 1.56 | 1.56 |
| Candida albicans NHL 4019 | 12.5 | 12.5 |
| Candida albicans Yu-1200 | 12.5 | 25.0 |
| Saccharomyces cerevisiae ATCC 9763 | 0.025 | 12.5 |
| Saccharomyces ruxii 6507 | 0.39 | 0.78 |
| Aspergillus niger ATCC 9642 | 0.025 | 0.10 |
| Penicillium chrysogenum ATCC 6010 | 3.12 | ·6.25 |
| Trichophyton mentagrophytes QM 248 | 0.006 | <0.006 |
| Trichophyton mentagrophytes IFO 5812 | <0.006 | <0.006 |
| Trichophyton tonsurans IFO 5928 | <0.006 | <0.006 |
| Trichophyton rubrum NHL J | <0.006 | <0.006 |
| Microsporum gypseum IFO 8231 | 0.006 | <0.006 |
| Microsporum audounii IFO 6074 | <0.006 | <0.006 |
| Microsporum cookei IFO 8303 | 0.012 | 0.10 |
| Epidermophyton floccosum IFO 9045 | 0.10 | 0.20 |
| Aspergillus oryzae IMF 4014 | <0.006 | <0.006 |
| Cladosporium fulvum IAM 5006 | 0.78 | 1.56 |
| Fusarium moniliforme IAM 5062 | 3.12 | 6.25 |
| Helminthosporium sesamum IAM 5012 | <0.006 | <0.006 |
| Pyricularia oryzae IAM 5016 | <0.006 | <0.006 |
| Debaryomyces kloeckeri IFO 0015 | 3.12 | 12.5 |
| Gibberella fujikuroi IAM 8046 | 0.78 | 1.56 |

Compound (I) prepared as fully described above has strong antimicrobial activity, especially against those fungi belonging to the genera Candida, Trichophyton, Microsporum, Epidermorphyton, and the like, as well as Gram-positive bacteria, and thus is useful as a antimicrobial agent.

Other features of the invention will become apparent in the course of the following description of the exemplary embodiments which are given for illustration of the invention and are not intended to be limiting thereof.

EXAMPLES

Example 1

Preparation of 1-[2-hydroxy-2-(2-hydroxyphenyl)pentyl]imidazole (Compound 18)

To a tetrahydrofuran solution of Grignard reagent prepared from 73 mg of magnesium and 369 mg of n-propyl bromide, 202 mg of 1-(2-hydroxyphenacyl) imidazole (II) was added dropwise under ice-cooled conditions while stirring, and the mixture was refluxed for 2 hours. After ice-cooling, an aqueous solution of ammonium chloride was added to the mixture to decompose the surplus amount of the Grignard reagent and addition salts produced in the reaction. Extraction with chloroform was performed on this mixture and the chloroform layer was washed with water, followed by drying over anhydrous magnesium sulfate. The extract thus obtained was purified by means of silica gel column chromatography (eluent: chloroform) to produce 70 mg of the title compound at a yield of 29%.

Example 2

Preparation of 1-[2-hydroxy-2-(2-ethoxyphenyl)pentyl]imidazole (Compound 20)

34 mg of 1-[2-hydroxy-2-(2-hydroxyphenyl)pentyl]imidazole (Compound 18) was dissolved into 10 ml of dimethylformamide, and 33 mg of ethyl iodide and 10 mg of sodium hydroxide was added to this solution. The mixture was stirred at room temperature for 20 hours. The reaction mixture, after being charged into ice water, was subjected to extraction with ether. The ether layer was then washed with water, followed by drying over anhydrous magnesium sulfate. The extract thus obtained was purified by means of silica gel column chromatography (eluent: methylene chloride) to produce 22 mg of the title compound at a yield of 58%.

Example 3

Reactions were carried out in the same manner as in Examples 1 and 2 to synthesize the compounds listed in Table 2. The compounds produced in Examples 1 and 2 are also listed in the table.

TABLE 2

| Compound No. | R₁ | R₂ | Appearance | IR(νcm⁻¹) | NMR(CDCl₃) δ(ppm) |
|---|---|---|---|---|---|
| 1 | CH₃ | H | White crystals m.p.163–165° C. | 3350, 2350, 1510, 1230 | 1.53 (s, 3H), 4.10 (d, 1H), 4.30 (d, 1H), 6.6–7.4 (m, 7H), 8.75 (s, 2H) |
| 2 | CH₃ | C₂H₅ | Oily substance | 3200, 3000, 1450, 1230 | 1.47 (t, 3H), 1.53 (s, 3H), 4.06 (q, 2H), 4.27 (s, 2H), 6.6–7.5 (m, 7H) |
| 3 | CH₃ | C₃H₇ | Oily substance | 3150, 2960, 1440, 1220 | 1.06 (t, 3H), 1.53 (s, 3H), 1.7–2.1 (m, 2H), 3.98 (t, 2H), 4.27 (s, 2H), 4.36 (s, 1H), 6.6–7.4 (m, 7H) |
| 4 | CH₃ | C₄H₉ | Oily substance | 3150, 2940, 1445, 1225 | 0.7–1.1 (t-like, 3H), 1.1–2.1 (m, 4H), 1.54 (s, 3H), 4.06 (t, 2H), 3.9–4.2 (m, 1H), 4.31 (s, 2H), 6.6–7.4 (m, 7H) |
| 5 | CH₃ | C₅H₁₁ | Oily substance | 3150, 2950, 1445, 1230 | 0.7–1.0 (t-like, 3H), 1.1–2.1 (m, 6H), 1.47 (s, 3H), 3.97 (t, 2H), 4.24 (s, 2H), 4.35 (s, 1H), 6.6–7.4 (m, 7H) |
| 6 | CH₃ | C₆H₁₃ | Oily substance | 3150, 2950, 1450, 1230 | 0.7–1.1 (t-like, 3H), 1.1–2.3 (m, 8H), 1.52 (s, 3H), 4.00 (t, 2H), 4.28 (s, 2H), 4.90 (s, 1H), 6.6–7.4 (m, 7H) |
| 7 | CH₃ | C₇H₁₅ | Oily substance | 3150, 2950, 1450, 1230 | 0.7–1.1 (t-like, 3H), 1.1–2.1 (m, 10H), 1.53 (s, 3H), 4.00 (t, 2H), 4.30 (s, 2H), 5.30 (s, 1H), 6.6–7.5 (m, 7H) |
| 8 | CH₃ | C₈H₁₇ | Oily substance | 3150, 2950, 1450, 1235 | 0.6–1.0 (t-like, 3H), 1.0–2.0 (m, 12H), 1.53 (s, 3H), 4.02 (t, 2H), 4.31 (s, 2H), 4.75 (s, 1H), 6.5–7.5 (m, 7H) |
| 9 | C₂H₅ | H | White crystals m.p. 94–96° C. | 3140, 2980, 1450, 1240 | 0.85 (t, 3H), 1.4–2.3 (m, 2H), 4.16 (d, 1H), 4.18 (d, 1H), 6.6–7.4 (m, 7H), 8.6–9.0 (m, 2H) |
| 10 | C₂H₅ | CH₃ | White crystals m.p.155–157° C. | 3200, 2950, 1445, 1240 | 0.74 (t, 3H), 1.3–2.4 (m, 2H), 3.77 (s, 3H), 3.97 (s, 1H), 4.20 (d, 1H), 4.27 (d, 1H), 6.5–7.4 (m, 7H) |
| 11 | C₂H₅ | C₂H₅ | Oily substance | 3180, 3000, 1450, 1240 | 0.74 (t, 3H), 1.43 (t, 3H), 1.6–2.5 (m, 2H), 4.06 (q, 2H), 4.26 (d, 1H), 4.33 (s, 1H), 4.40 (d, 1H), 6.6–7.5 (m, 7H) |
| 12 | C₂H₅ | C₃H₇ | Oily substance | 3180, 2980, 1450, 1230 | 0.73 (t, 3H), 1.04 (t, 3H), 1.3–2.6 (m, 4H), 3.97 (t, 2H), 4.16 (d, 1H), 4.28 (d, 1H), 4.33 (d, 1H), 6.6–7.5 (m, 7H) |
| 13 | C₂H₅ | C₄H₉ | Oily substance | 3180, 2980, 1450, 1240 | 0.72 (t, 3H), 0.97 (t, 3H), 1.1–2.6 (m, 6H), 4.00 (t, 2H), 4.27 (d, 1H), 4.36 (d, 1H), 4.59 (s, 1H), 6.6–7.5 (m, 7H) |
| 14 | C₂H₅ | C₅H₁₁ | Oily substance | 3160, 2950, 1450, 1230 | 0.74 (t, 3H), 0.93 (t, 3H), 1.1–2.6 (m, 6H), 3.99 (t, 2H), 4.27 (d, 1H), 4.38 (d, 1H), 4.47 (s, 1H), 6.6–7.5 (m, 7H) |
| 15 | C₂H₅ | C₆H₁₃ | Oily substance | 3190, 2960, 1450, 1235 | 0.77 (t, 3H), 0.90 (t, 3H), 1.1–2.6 (m, 10H), 3.97 (t, 2H), 4.23 (s, 1H), 4.29 (d, 1H), 4.35 (d, 1H), 6.6–7.5 (m, 7H) |
| 16 | C₂H₅ | C₇H₁₅ | Oily substance | 3180, 2950, 1455, 1235 | 0.73 (t, 3H), 0.7–1.1 (t-like, 3H), 1.1–2.6 (m, 12H), 4.00 (t, 2H), 4.28 (d, 1H), 4.40 (d, 1H), 4.77 (s, 1H), 6.6–7.6 (m, 7H) |
| 17 | C₂H₅ | C₈H₁₇ | Oily substance | 3180, 2960, 1455, 1235 | 0.73 (t, 3H), 0.7–1.0 (t-like, 3H), 1.0–2.5 (m, 14H), 4.00 (t, 2H), 4.28 (d,1H), 4.37 (d, 1H), 4.67 (s, 1H), 6.5–7.5 (m, 7H) |
| 18 | C₃H₇ | H | Oily substance | 3140, 2980, 1450, 1240 | 0.7–1.1 (t-like, 3H), 1.1–2.3 (m, 4H), 4.06 (d, 1H), 4.23 (d, 1H), 6.6–7.4 (m, 7H), 8.0–8.4 (m, 2H) |
| 19 | C₃H₇ | CH₃ | Oily substance | 3200, 2980, 1440, 1240 | 0.7–1.1 (t-like, 3H), 1.1–2.5 (m, 4H), 3.82 (s, 3H), 3.83 (s, 1H), 4.20 (d, 1H), 4.37 (d, 1H), 6.6–7.5 (m, 7H) |
| 20 | C₃H₇ | C₂H₅ | Oily substance | 3160, 2980, 1450, 1235 | 0.7–1.0 (t-like, 3H), 1.0–1.8 (m, 4H), 1.42 (t, 3H), 4.10 (q, 2H), 4.28 (d, 1H), 3.8–4.2 (m, 1H), 4.46 (d, 1H), 6.6–7.4 (m, 7H) |
| 21 | C₃H₇ | C₃H₇ | Oily substance | 3160, 2980, 1455, 1235 | 0.7–1.0 (t-like, 3H), 1.05 (t, 3H), 1.2–2.5 (m, 6H), 3.5–3.7 (m, 1H), 3.97 (t, 2H), 4.19 (d, 1H), 4.40 (d, 1H), 6.6–7.6 (m, 7H) |
| 22 | C₃H₇ | C₄H₉ | Oily substance | 3160, 2990, 1455, 1235 | 0.7–1.0 (t-like, 3H), 1.00 (t, 3H), 1.1–2.3 (m, 8H), 3.8–4.2 (m, 1H), 4.07 (t, 2H), 4.27 (d, 1H), 4.42 (d, 1H), 6.6–7.4 (m, 7H) |
| 23 | C₃H₇ | C₅H₁₁ | Oily substance | 3180, 2980, 1455, 1235 | 0.7–1.1 (t-like, 6H), 1.1–2.5 (m, 10H), 4.01 (t, 2H), 4.20 (d, 1H), 4.34 (s, 1H), 4.47 (d, 1H), 6.6–7.5 (m, 7H) |
| 24 | C₃H₇ | C₆H₁₃ | Oily substance | 3180, 2990, 1455, 1235 | 0.6–1.1 (t-like, 6H), 1.1–2.5 (m, 12H), 3.99 (t, 2H), 4.20 (d, 1H), 4.43 (d, 1H), 4.74 (s, 1H), 6.6–7.5 (m, 7H) |
| 25 | C₃H₇ | C₇H₁₅ | Oily substance | 3170, 2960, 1455, 1235 | 0.6–1.0 (t-like, 6H), 1.0–2.3 (m, 14H), 4.01 (t, 2H), 4.31 (s, 1H), 4.33 (d, 1H), 4.38 (d, 1H), 6.6–7.6 (m, 7H) |
| 26 | C₃H₇ | C₈H₁₇ | Oily substance | 3170, 2950, | 0.6–1.0 (t-like, 6H), 1.0–2.3 (m 16H), 4.00 (t, 2H), 4.06 |

TABLE 2-continued

| Compound No. | R₁ | R₂ | Appearance | IR(νcm⁻¹) | NMR(CDCl₃) δ(ppm) |
|---|---|---|---|---|---|
| 27 | C₄H₉ | H | Oily substance | 1455, 1235 3200, 2970, 1455, 1240 | (s, 1H), 4.24 (d, 1H), 4.33 (d, 1H), 6.5–7.5 (m, 7H) 0.7–1.1 (t-like, 3H), 1.1–2.2 (m, 6H), 3.5–3.8 (m, 2H), 4.15 (d, 1H), 4.22 (d, 1H), 6.4–7.3 (m, 7H) |
| 28 | C₄H₉ | CH₃ | Oily substance | 3170, 2980, 1440, 1240 | 0.77 (t, 3H), 4.25 (d, 1H), 3.80 (s, 3H), 3.9–4.2 (m, 1H), 4.18 (d, 1H), 4.25 (d, 1H), 6.5–7.4 (m, 7H) |
| 29 | C₄H₉ | C₂H₅ | Oily substance | 3180, 2980, 1450, 1235 | 0.80 (t, 3H), 1.0–2.4 (m, 6H), 1.44 (t, 3H), 4.06 (q, 2H), 4.10 (s, 1H), 4.25 (d, 1H), 4.33 (d, 1H), 6.5–7.4 (m, 7H) |
| 30 | C₄H₉ | C₃H₇ | Oily substance | 3180, 2980, 1450, 1235 | 0.80 (t, 3H), 1.09 (t, 3H), 4.38 (d, 1H), 6.5–7.5 (m, 7H), 4.28 (d, 1H), 4.36 (s, 1H), 1.0–2.4 (m, 8H), 3.97 (t, 2H) |
| 31 | C₄H₉ | C₄H₉ | Oily substance | 3170, 2970, 1450, 1235 | 0.80 (t, 3H), 1.00 (t, 3H), 1.1–2.6 (m, 10H), 4.01 (t, 2H), 4.29 (d, 1H), 4.38 (d, 1H), 4.80 (s, 1H), 6.5–7.5 (m, 7H) |
| 32 | C₄H₉ | C₅H₁₁ | Oily substance | 3170, 2980, 1450, 1235 | 0.87 (t, 3H), 0.92 (t, 3H), 1.0–2.5 (m, 12H), 4.00 (t, 2H), 4.28 (d, 1H), 4.38 (d, 1H), 4.84 (s, 1H), 6.5–7.5 (m, 7H) |
| 33 | C₄H₉ | C₆H₁₃ | Oily substance | 3170, 2950, 1455, 1235 | 0.7–1.1 (t-like, 6H), 1.1–2.5 (m, 14H), 4.02 (t, 2H), 4.30 (d, 1H), 4.39 (d, 1H), 4.47 (s, 1H), 6.6–7.6 (m, 7H) |
| 34 | C₄H₉ | C₇H₁₅ | Oily substance | 3170, 2950, 1455, 1235 | 0.6–1.0 (t-like, 6H), 1.0–2.5 (m, 16H), 4.00 (t, 2H), 4.00 (s, 1H), 4.25 (d, 1H), 4.34 (d, 1H), 6.5–7.5 (m, 7H) |
| 35 | C₄H₉ | C₈H₁₇ | Oily substance | 3170, 2950, 1450, 1235 | 0.6–1.1 (t-like, 6H), 1.1–2.4 (m, 18H), 3.80 (s, 1H), 4.00 (t, 2H), 4.24 (d, 1H), 4.35 (d, 1H), 6.6–7.5 (m, 7H) |
| 36 | C₅H₁₁ | H | White crystals m.p. 148–150° C. | 3190, 2960, 1450, 1235 | 0.7–1.0 (t-like, 3H), 1.0–2.5 (m, 8H), 4.27 (d, 1H), 4.46 (d, 1H), 6.6–7.6 (m, 9H) |
| 37 | C₅H₁₁ | C₂H₅ | Oily substance | 3200, 2990, 1455, 1245 | 0.6–1.0 (t-like, 3H), 1.0–2.5 (m, 8H), 1.43 (t, 3H), 3.86 (s, 1H), 4.05 (q, 2H), 4.25 (d, 1H), 4.34 (d, 1H), 6.6–7.5 (m, 7H) |
| 38 | C₅H₁₁ | C₃H₇ | Oily substance | 3200, 2980, 1450, 1235 | 0.7–1.0 (t-like, 6H), 1.0–2.5 (m, 10H), 3.96 (t, 2H), 4.21 (s, 1H), 4.27 (d, 1H), 4.34 (d, 1H), 6.6–7.5 (m, 7H) |
| 39 | C₅H₁₁ | C₄H₉ | White crystals m.p. 74–76° C. | 3150, 2940, 1440, 1225 | 0.6–1.0 (t-like, 6H), 1.0–2.5 (m, 12H), 4.01 (t, 2H), 4.28 (d, 1H), 4.38 (d, 1H), 4.83 (s, 1H), 6.5–7.5 (m, 7H) |
| 40 | C₅H₁₁ | C₅H₁₁ | White crystals m.p. 74–76° C. | 3160, 2940, 1450, 1240 | 0.6–1.0 (t-like, 6H), 1.0–2.5 (m, 14H), 4.02 (t, 2H), 4.31 (d, 1H), 4.40 (d, 1H), 4.83 (s, 1H), 6.5–7.5 (m, 7H) |
| 41 | C₅H₁₁ | C₆H₁₃ | Oily substance | 3200, 2980, 1455, 1240 | 0.6–1.0 (t-like, 6H), 1.0–2.5 (m, 16H), 4.02 (t, 2H), 4.27 (d, 1H), 4.38 (d, 1H), 4.66 (s, 1H), 6.4–7.5 (m, 7H) |
| 42 | C₅H₁₁ | C₇H₁₅ | Oily substance | 3200, 2960, 1455, 1240 | 0.6–1.1 (t-like, 6H), 1.1–2.5 (m, 18H), 4.01 (t, 2H), 4.28 (d, 1H), 4.38 (d, 1H), 4.67 (s, 1H), 6.5–7.5 (m, 7H) |
| 43 | C₅H₁₁ | C₈H₁₇ | Oily substance | 3200, 2960, 1455, 1235 | 0.5–1.0 (t-like, 6H), 1.0–2.5 (m, 20H), 4.00 (t, 2H), 4.28 (d, 1H), 4.38 (d, 1H), 4.65 (s, 1H), 6.4–7.5 (m, 7H) |
| 44 | C₃H₇ | —CH₂—C₆H₅ | Oily substance | 3200, 2960, 1455, 1230 | 0.6–1.0 (t-like, 3H), 1.0–2.5 (m, 4H), 3.46 (brs, 1H), 4.20 (d, 1H), 4.30 (d, 1H), 5.09 (s, 2H), 6.5–7.6 (m, 7H), 7.40 (s, 5H) |
| 45 | C₃H₇ | —CH₂—C₆H₄Cl | White crystals m.p. 145–146° C. | 3200, 2980, 1490, 1235 | 0.6–1.0 (t-like, 3H), 1.0–2.5 (m, 4H), 3.85 (brs, 1H), 4.23 (d, 1H), 4.33 (d, 1H), 5.04 (s, 2H), 6.5–7.6 (m, 11H) |

TABLE 2-continued

| Compound No. | $R_1$ | $R_2$ | Appearance | IR($v$cm$^{-1}$) | NMR(CDCl$_3$) $\delta$(ppm) |
|---|---|---|---|---|---|
| 46 | $C_3H_7$ |  —CH$_2$— (4-Cl-phenyl) | Oily substance | 3190, 2990, 1500, 1230 | 0.6–1.0 (t-like, 3H), 1.0–2.5 (m, 4H), 4.18 (d, 1H), 4.32 (brs, 1H), 4.35 (d, 1H), 5.03 (s, 2H), 6.5–8.0 (m, 7H), 7.36 (s, 4H) |
| 47 | $C_3H_7$ | 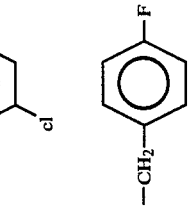 —CH$_2$— (3,4-diCl-phenyl) | White crystals m.p. 137–138° C. | 3130, 2970, 1490, 1235 | 0.6–1.0 (t-like, 3H), 1.0–2.5 (m, 4H), 3.56 (brs, 1H), 4.20 (d, 1H), 4.36 (d, 1H), 5.13 (s, 2H), 6.5–7.5 (m, 10H) |
| 48 | $C_3H_7$ |  —CH$_2$— (4-F-phenyl) | White crystals m.p. 127–128° C. | 3130, 2970, 1510, 1225 | 0.6–1.0 (t-like, 3H), 1.0–2.5 (m, 4H), 3.73 (s, 1H), 3.73 (s, 1H), 4.20 (d, 1H), 4.30 (d, 1H), 5.02 (s, 2H), 6.5–7.7 (m, 11H) |
| 49 | $C_3H_7$ |  —CH$_2$— (3,4-diF-phenyl) | Oily substance | 3150, 2990, 1510, 1230 | 0.6–1.0 (t-like, 3H), 1.0–2.4 (m, 4H), 3.64 (s, 1H), 4.20 (d, 1H), 4.30 (d, 1H), 5.08 (s, 2H), 6.4–7.6 (m, 10H) |
| 50 | $C_3H_7$ | 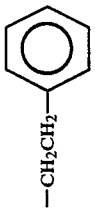 —CH$_2$CH$_2$— (phenyl) | Oily substance | 3100, 2940, 1445, 1225 | 0.6–1.0 (t-like, 3H), 1.0–2.1 (m, 4H), 2.7–3.0 (m, 1H), 3.14 (t, 2H), 4.16 (t, 2H), 4.0–4.4 (m, 2H), 6.5–7.6 (m, 12H) |
| 51 | $C_3H_7$ |  —CH$_2$CH$_2$— (4-Cl-phenyl) | Oily substance | 3300, 2960, 1495, 1240 | 0.6–1.0 (t-like, 3H), 1.0–2.1 (m, 4H), 2.7–3.0 (m, 1H), 3.10 (t, 2H), 4.18 (t, 2H), 4.0–4.4 (m, 2H), 6.5–7.6 (m, 11H) |
| 52 | $C_3H_7$ | 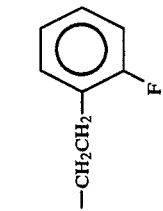 —CH$_2$CH$_2$— (2-F-phenyl) | Oily substance | 3130, 2980, 1495, 1230 | 0.6–1.0 (t-like, 3H), 1.0–2.2 (m, 4H), 3.0–3.2 (m, 1H), 3.18 (t, 2H), 4.20 (t, 2H), 4.0–4.4 (m, 2H), 6.5–7.6 (m, 11H) |

TABLE 2-continued

| Compound No. | $R_1$ | $R_2$ | Appearance | IR(vcm$^{-1}$) | NMR(CDCl$_3$) δ(ppm) |
|---|---|---|---|---|---|
| 53 | C$_3$H$_7$ | —CH$_2$CH$_2$—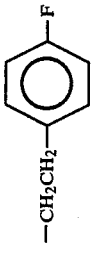F | Oily substance | 3150, 2960, 1510, 1230 | 0.6–1.0 (t-like, 3H), 1.0–2.2 (m, 4H), 2.7–3.0 (m, 1H), 3.12 (t, 2H), 4.20 (t, 2H), 4.0–4.4 (m, 2H), 6.5–7.6 (m, 11H) |
| 54 | C$_3$H$_7$ | —CH(CH$_3$)$_2$ | White crystals m.p. 126–128° C. | 3160, 2990, 1490, 1230 | 0.6–1.0 (t-like, 3H), 1.0–2.5 (m, 4H), 1.33 (d, 3H), 1.43 (d, 3H), 3.49 (s, 1H), 4.23 (d, 1H), 4.34 (d, 1H), 4.4–4.9 (m, 1H), 6.5–7.4 (m, 7H) |
| 55 | C$_3$H$_7$ | —CH$_2$CH(CH$_3$)$_2$ | Oily substance | 3180, 2990, 1475, 1235 | 0.6–1.0 (t-like, 3H), 1.0–2.5 (m, 5H), 1.08 (d, 6H), 3.79 (d, 2H), 4.10 (s, 1H), 4.27 (d, 1H), 4.37 (d, 1H), 6.5–7.5 (m, 7H) |
| 56 | C$_3$H$_7$ | —(CH$_2$)$_2$CH(CH$_3$)$_2$ | Oily substance | 3200, 2980, 1455, 1235 | 0.6–1.0 (t-like, 3H), 0.99 (d, 6H), 1.0–2.3 (m, 7H), 3.70 (s, 1H), 4.03 (t, 2H), 4.25 (d, 1H), 4.35 (d, 1H), 6.5–7.4 (m, 7H) |
| 57 | C$_3$H$_7$ | —CH$_2$CH$_2$Cl | White crystals m.p. 123–125° C. | 3140, 2970, 1445, 1235 | 0.6–1.0 (t-like, 3H), 1.0–2.6 (m, 4H), 3.8–4.1 (m, 2H), 4.2–4.5 (m, 3H), 4.30 (d, 1H), 4.43 (d, 1H), 6.7–7.6 (m, 7H) |
| 58 | C$_3$H$_7$ | —CH$_2$CH$_2$F | Oily substance | 3180, 2980, 1445, 1235 | 0.6–1.0 (t-like, 3H), 1.0–2.6 (m, 4H), 4.05 (s, 1H), 3.9–4.5 (m, 2H), 4.33 (d, 1H), 4.39 (d, 1H), 4.67 (dt, 2H), 6.6–7.6 (m, 7H) |
| 59 | CH$_3$ | C$_9$H$_{19}$ | Oily substance | 3150, 2940, 1450, 1230 | 0.7–1.1 (t-like, 3H), 1.1–2.3 (m, 14H), 1.53 (s, 3H), 4.02 (t, 2H), 4.30 (s, 2H), 4.66 (s, 1H), 6.6–7.5 (m, 7H) |
| 60 | CH$_3$ | C$_{10}$H$_{21}$ | Oily substance | 3150, 2920, 1450, 1230 | 0.7–1.1 (t-like, 3H), 1.1–2.5 (m, 16H), 1.55 (s, 3H), 4.03 (t, 2H), 4.31 (s, 2H), 4.45 (s, 1H), 6.6–7.5 (m, 7H) |
| 61 | CH$_3$ | C$_{11}$H$_{23}$ | Oily substance | 3160, 2920, 1440, 1230 | 0.7–1.1 (t-like, 3H), 1.1–2.5 (m, 18H), 1.54 (s, 3H), 4.02 (t, 2H), 4.03 (s, 1H), 4.28 (s, 2H), 6.6–7.5 (m, 7H) |
| 62 | C$_3$H$_7$ | —CH$_2$—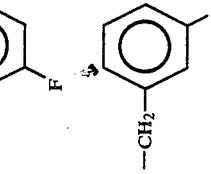 | Oily substance | 3160, 2950, 1450, 1230 | 0.6–1.0 (t-like, 3H), 1.0–2.5 (m, 4H), 4.26 (d, 1H), 4.33 (d, 1H), 4.5–4.7 (brs, 1H), 5.14 (s, 2H), 6.5–7.6 (m, 11H) |
| 63 | C$_3$H$_7$ | —CH$_2$—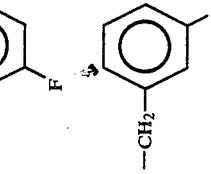 | White crystals m.p. 143–144° C. | 3150, 2950, 1450, 1230 | 0.6–1.0 (t-like, 3H), 1.0–2.5 (m, 4H), 4.23 (d, 1H), 4.33 (d, 1H), 4.2–4.3 (brs, 1H), 5.09 (s, 2H), 6.5–7.6 (m, 11H) |
| 64 | C$_3$H$_7$ |  | Oily substance | 3150, 2950, 1450, 1230 | 0.7–3.0 (m, 11H), 3.8–4.3 (m, 2H), 4.2–4.6 (m, 2H), 6.5–7.7 (m, 7H) |
| 65 | C$_3$H$_7$ | —CH$_2$— | Oily substance | 3150, 2950, 1450, 1230 | 0.3–2.6 (m, 12H), 3.82 (d, 2H), 4.27 (d, 1H), 4.41 (d, 1H), 4.2–4.5 (brs, 1H), 6.5–7.5 (m, 7H) |
| 66 | C$_3$H$_7$ |  | Oily substance | 3150, 2950, 1450, 1230 | 0.2–2.7 (m, 15H), 3.8–4.2 (m, 1H), 4.29 (d, 1H), 4.40 (d, 1H), 4.9–5.3 (m, 1H), 6.6–7.7 (m, 7H) |

TABLE 2-continued

| Compound No. | R₁ | R₂ | Appearance | IR(νcm⁻¹) | NMR(CDCl₃) δ(ppm) |
|---|---|---|---|---|---|
| 67 | C₃H₇ | —(CH₂)₃CH(CH₃)₂ | Oily substance | 3150, 2950, 1450, 1230 | 0.6–1.1 (t-like, 3H), 0.95 (d, 6H), 1.1–2.5 (m, 9H), 3.4–3.7 (brs, 1H), 4.02 (t, 2H), 4.27 (d, 1H), 4.39 (d, 1H), 6.6–7.5 (m, 7H) |
| 68 | C₃H₇ | 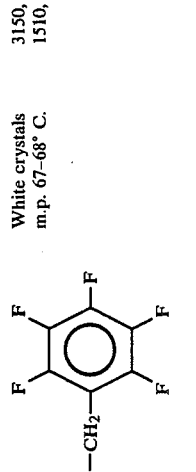 | White crystals m.p. 67–68° C. | 3150, 2960, 1510, 1220 | 0.7–1.1 (t-like, 3H), 1.1–2.3 (m, 4H), 2.6–3.0 (brs, 1H), 4.17 (d, 1H), 4.30 (d, 1H), 5.1–5.4 (brs, 2H), 6.5–7.5 (m, 7H) |
| 69 | C₃H₇ | —(CH₂)₃— | Oily substance | 3150, 2950, 1450, 1230 | 0.6–1.0 (t-like, 3H), 1.0–2.5 (m, 4H), 2.16 (t, 2H), 2.7–3.0 (m, 2H), 2.9–3.2 (m, 1H), 4.02 (t, 2H), 4.28 (d, 1H), 4.39 (d, 1H), 6.7–7.5 (m, 7H), 7.24 (s, 5H) |
| 70 | —CH(CH₃)₂ | C₃H₇ | White crystals m.p. 89–91° C. | 3140, 2960, 1440, 1220 | 0.71 (d, 3H), 1.09 (d, 3H), 0.8–1.3 (t-like, 3H), 1.5–2.1 (m, 2H), 2.3–2.8 (m, 1H), 3.4–3.7 (brs, 1H), 3.7–4.1 (t-like, 2H), 4.23 (d, 1H), 4.60 (d, 1H), 6.5–7.5 (m, 7H) |
| 71 | —CH(CH₃)₂ | C₄H₉ | White crystals m.p. 119–121° C. | 3150, 2970, 1440, 1240 | 0.70 (d, 3H), 1.06 (d, 3H), 0.7–1.2 (t-like, 3H), 1.2–2.1 (m, 4H), 2.2–2.9 (m, 1H), 3.7–4.1 (t-like, 2H), 4.1–4.3 (brs, 1H), 4.25 (d, 1H), 4.61 (d, 1H), 6.5–7.4 (m, 7H) |
| 72 | —CH(CH₃)₂ | C₅H₁₁ | White crystals m.p. 122–123° C. | 3150, 2970, 1440, 1230 | 0.73 (d, 3H), 1.09 (d, 3H), 0.7–1.1 (t-like, 3H), 1.1–2.2 (m, 6H), 2.3–3.0 (m, 1H), 3.6–4.1 (m, 3H), 4.27 (d, 1H), 4.61 (d, 1H), 6.5–7.4 (m, 7H) |
| 73 | —CH(CH₃)₂ | C₆H₁₃ | White crystals m.p. 103–105° C. | 3150, 2960, 1440, 1220 | 0.71 (d, 3H), 1.09 (d, 3H), 0.7–1.1 (t-like, 3H), 1.1–2.3 (m, 8H), 2.3–3.0 (m, 1H), 3.5–3.8 (brs, 1H), 3.7–4.1 (t-like, 2H), 4.23 (d, 1H), 4.60 (d, 1H), 6.5–7.5 (m, 7H) |
| 74 | —CH(CH₃)₂ | 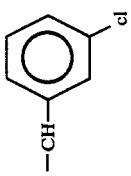 | White crystals m.p. 102–104° C. | 3140, 2970, 1440, 1220 | 0.72 (d, 3H), 1.07 (d, 3H), 2.2–3.0 (m, 1H), 3.3–3.6 (brs, 1H), 4.23 (d, 1H), 4.56 (d, 1H), 5.01 (s, 2H), 6.4–7.5 (m, 11H) |

Obviously, numerous modifications and variations of the present invention are possible in light of the above teachings. It is therefore to be understood that the scope of the appended claims, the invention may be practiced otherwise than as specifically described herein.

What is claimed as new and desired to be secured by letters patent is:

1. An imidazole derivative represented by the following formula (I):

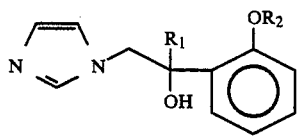

wherein $R_1$ represents an alkyl group, and $R_2$ represents a hydrogen atom or a nonheterocyclic aralkyl group which may have a substituent on the aryl moiety; or an acid adduct thereof.

2. The imidazole derivative of claim 1, wherein $R_1$ is selected from the group consisting of methyl, ethyl, n-propyl, i-propyl, n-butyl, i-butyl, sec-butyl, t-butyl, pentyl, hexyl, octyl, and cyclopropyl.

3. The imidazole derivative of claim 1, wherein $R_2$ is selected from the group consisting of phenylalkyl and naphthylalkyl.

4. The imidazole derivative of claim 1, wherein said substituent on the aryl moiety is selected from the group consisting of a halogen atom, a lower alkyl group, a lower alkoxy group, a lower alkanoyl group, and a cyano group.

* * * * *